US 6,584,338 B1

(12) United States Patent
Van Muiswinkel

(10) Patent No.: US 6,584,338 B1
(45) Date of Patent: Jun. 24, 2003

(54) DERIVING TIME-AVERAGED MOMENTS

(75) Inventor: Arianne M. C. Van Muiswinkel, Eindhoven (NL)

(73) Assignee: Koninklijke Philips Electronics N.V., Eindhoven (NL)

(*) Notice: Subject to any disclaimer, the term of this patent is extended or adjusted under 35 U.S.C. 154(b) by 0 days.

(21) Appl. No.: 09/701,628

(22) PCT Filed: Mar. 27, 2000

(86) PCT No.: PCT/EP00/02676
§ 371 (c)(1),
(2), (4) Date: Nov. 30, 2000

(87) PCT Pub. No.: WO00/60520
PCT Pub. Date: Oct. 12, 2000

(30) Foreign Application Priority Data

Mar. 30, 1999 (EP) ............................................. 99200994

(51) Int. Cl.[7] ................................................ A61B 5/05
(52) U.S. Cl. ...................................................... 600/419
(58) Field of Search ................................ 600/419, 407, 600/410; 324/306, 307, 308, 309, 310; 378/14

(56) References Cited

U.S. PATENT DOCUMENTS

| 4,149,247 | A | * | 4/1979 | Pavkovich et al. ............ 378/14 |
| 4,173,720 | A | * | 11/1979 | Geluk ........................ 382/131 |
| 5,150,292 | A | * | 9/1992 | Hoffmann et al. ........... 600/431 |
| 5,249,122 | A | * | 9/1993 | Stritzke ....................... 600/431 |
| 5,293,312 | A | * | 3/1994 | Waggener ..................... 378/14 |
| 5,396,418 | A | * | 3/1995 | Heuscher ...................... 378/15 |
| 5,570,018 | A | * | 10/1996 | Halse .......................... 324/309 |
| 5,687,726 | A | * | 11/1997 | Hoeft .......................... 600/431 |
| 5,720,921 | A | * | 2/1998 | Meserol ....................... 422/44 |
| 6,057,686 | A | * | 5/2000 | Van Den Brink et al. .. 324/309 |
| 6,331,777 | B1 | * | 12/2001 | Van Den Brink et al. .. 324/312 |
| 6,371,923 | B1 | * | 4/2002 | Roteliuk et al. ............ 600/526 |
| 6,421,549 | B1 | * | 7/2002 | Jacques ....................... 600/331 |
| 6,442,288 | B1 | * | 8/2002 | Haerer et al. ............... 382/128 |

OTHER PUBLICATIONS

"High Resolution Measurement of Cerebral Blood Flow using Intravascular Tracer Bolus Passages. Part I: Mathematical Apporach and Statistical Analysis" by Leif Ostergaard et al., in MRM 36(1996) pp. 715–725.

* cited by examiner

Primary Examiner—Teresa Walberg
Assistant Examiner—Daniel Robinson
(74) Attorney, Agent, or Firm—John Vodopia

(57) ABSTRACT

The invention relates to a method of deriving time-averaged moments of a convolution profile from dynamic input and arrival profiles. A convolutive relation exists between the arrival profile and the input profile. According to the invention the time-averaged moment of the convolution profile is calculated from time-averaged moments of the dynamic input and arrival profiles. The method is used notably for the study of perfusion effects by means of magnetic resonance imaging.

9 Claims, 1 Drawing Sheet

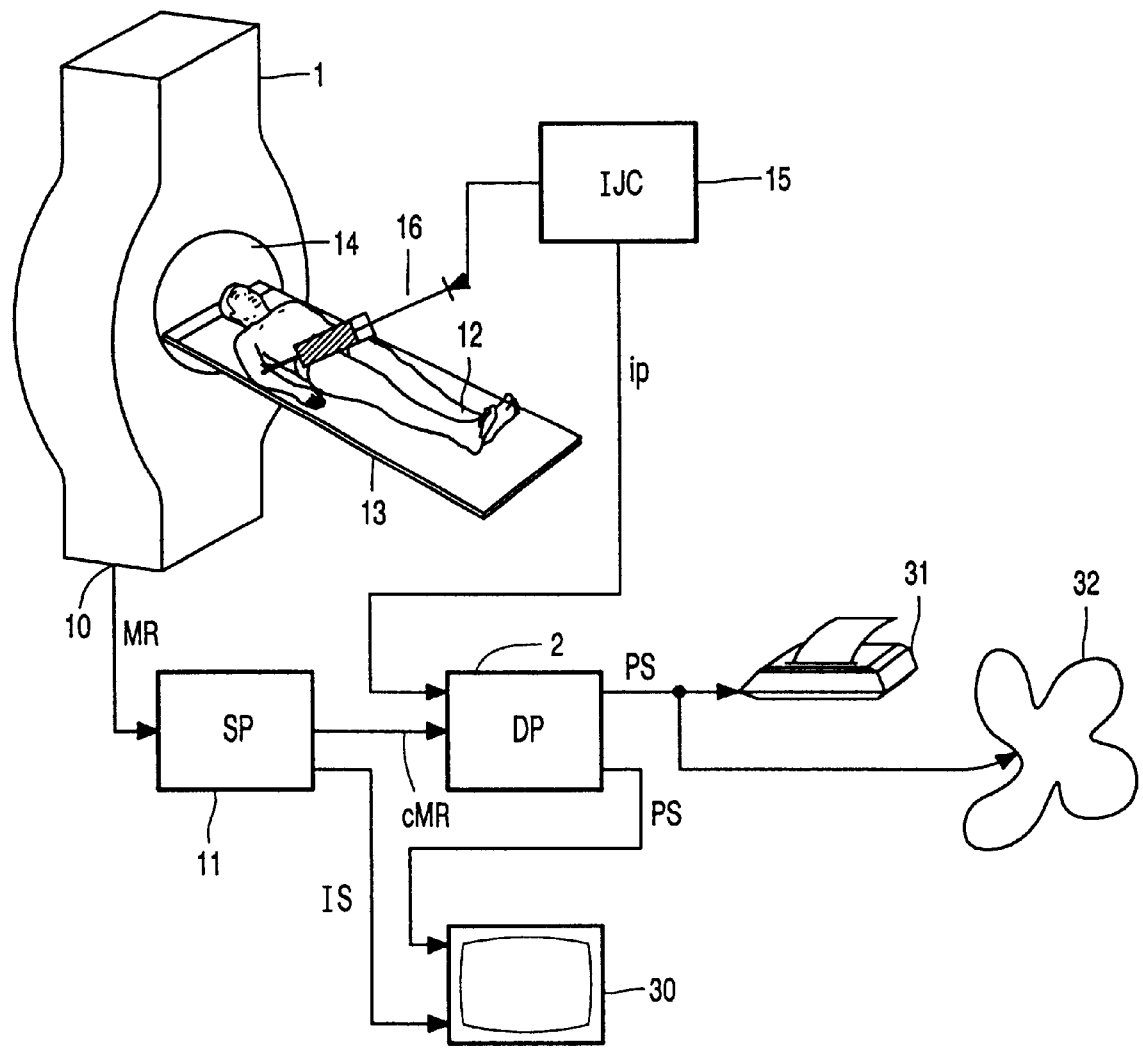

DERIVING TIME-AVERAGED MOMENTS

The invention relates to a method of deriving a time-averaged moment of a convolution profile from dynamic input and arrival profiles, the arrival profile being related to the input profile according to convolution with the convolution profile.

The article "High resolution measurement of cerebral blood flow using intravascular tracer bolus passages, part I: mathematical approach and statistical analysis" by L. Østergaard et al in MRM 36 (1996), 715–725, concerns the study of the blood flow through the brain. For such an examination a contrast agent is administered to a patient to be examined; for example, a contrast liquid is injected into a blood vessel. The concentration in which the contrast agent is fed, via an artery, to a part of the body of the patient to be examined, is determined in a time resolved manner. The time-dependent concentration of supplied contrast agent is referred to as the arterial input. Subsequently, the concentration of the contrast agent encountered in veins of the part of the body of the patient to be examined is determined in a time resolved manner. The time-dependent concentration of contrast agent in the artery is called the venous output in said article. A convolutive relation exists between the venous output and the arterial input. The convolution kernel is then the distribution of transit times through the network of blood vessels connecting the artery via which the contrast agent is supplied to veins in which the contrast agent is encountered somewhat later. This distribution of transit times is referred to as the transport function.

A method of the kind disclosed in the heading of Claim 1 is known from the cited article by L. Østergaard et al.; therein, the arterial input and the venous output are examples of the dynamic input profile and the arrival profile, respectively, and the transport function is an example of the convolution profile. According to the known method it is necessary to deconvolute the venous output so as to determine the transport function. The average transit time of the contrast medium through the network of blood vessels and the time-dependent concentration of contrast agent in a selected volume (volume-of-interest) are calculated on the basis of the transport function.

For the known method to yield reliable results it is necessary to determine the arterial input particularly accurately. It has been found nevertheless that, even when the arterial input is extremely accurately measured, the reliability of the calculated results is rather disappointing. Moreover, the known method involves rather complex and time-consuming calculations.

It is an object of the invention to provide a method whereby perfusion quantities can be accurately determined in a simpler manner in comparison with the known method.

This object is achieved by means of a method according to the invention which is characterized in that:

- a time-averaged moment of a dynamic input profile and a time-averaged moment of a dynamic arrival profile are determined, and that
- the time-averaged moment of the convolution profile is calculated from the time-averaged moments of the dynamic input profile and the time-averaged moments of the dynamic arrival profile.

According to the invention the perfusion quantities are calculated from time-averaged moments of the dynamic input and arrival profiles. Such perfusion quantities represent the degree and speed of displacement of various liquids through the tissue, for example the brain of the patient to be examined, under the influence of an external effect. For example, they concern the flow of notably blood and cerebrospinal fluid through a network of arteries, veins and capillaries. The perfusion of blood and other liquids through notably the brain of the patient to be examined can be studied quantitatively on the basis of values of perfusion quantities. In order to determine the values of the perfusion quantities, for example the dynamic input and arrival profiles are measured in a time resolved manner. Such dynamic input and arrival profiles are preferably measured with a temporal resolution of 2 s or less; this means that liquid flow variations which take place at a time scale of a few seconds are reliably measured. It has been found that the perfusion quantities can be calculated from various time-averaged moments of the convolution profile. Notably deconvolution is thus avoided and surprisingly simple calculations still yield a reliable, accurate result for the perfusion quantities. The invention is based on the recognition of the fact that the perfusion quantities are simply related to time-averaged moments of the arrival profile and that the convolution relation between the arrival profile and the input profile is equivalent to an algebraic relation between the Laplace transforms of the input and arrival profiles. This means notably that a simple algebraic relation exists between the time averages of the input and arrival profiles. Moreover, a causal relation exists between the arrival profile and the input profile; this is because contrast agent will appear in the veins of the patient only after contrast agent has been introduced into an artery. As a result of this causal relation, comparatively simple algebraic relations exist between the $N^{th}$-order time-averaged moments of the arrival profile on the one side and the $k^{th}$-order time-averaged moments of the input profile and the $k^{th}$ order time-averaged moments of the convolution profile on the other side, k and N being natural numbers and k being smaller than N. Thus, the perfusion quantities can be calculated by means of simple, notably algebraic operations. It has been found notably that the calculation of the perfusion quantities requires only rational functions, being polynomials or fractions whose numerator and denominator themselves are polynomials of the time-averaged moments of the input, arrival and convolution profiles. It is very simple to calculate such rational functions quickly and accurately. Furthermore, in respect of the input and arrival profiles the calculation of the perfusion quantities requires only the time-averaged moments of the input and arrival profiles; notably an accurate time resolved determination of the variations in time of the input and arrival profiles will not be required. According to the invention it is in particular possible to dispense with a complex and time-consuming exact determination of the arterial input, an accurate result nevertheless being obtained for the perfusion quantities.

These and other aspects of the invention will be further elucidated on the basis of the following embodiments which are defined in the dependent Claims.

A first, particularly attractive application of the invention is the calculation of the mean transit time of the contrast agent, for example through a part of the network of blood vessels in the brain. According to the invention the average transit time is calculated as the difference between the time of input and the arrival time. The times of input and arrival are simply the same as the first time-averaged moments of the dynamic input profile and arrival profile, respectively. Using the value of the average transit time of the contrast agent through the network of blood vessels, it can be quantitatively checked whether or not the blood circulation in the relevant organ, such as the brain, is in order.

A second particularly advantageous application of the invention is the calculation of the transit fraction from the input and arrival volumes. According to the invention the transit fraction is calculated as the quotient of the arrival and input volumes. The arrival and input volumes are simply calculated as the time-averaged (zero-order moments) of the respective output and input profiles. The transit fraction is a quantitative indication as to which part of the supplied liquid, such as blood containing the contrast agent, has reached the part of the body of the patient to be examined. The transit fraction, for example, accurately and quantitatively indicates whether blood circulates in the relevant organ. Furthermore, the so-called "flow" can be readily calculated as the quotient of the transit fraction and the average transit time. The flow represents the quantity of liquid, such as blood with the contrast agent, which flows through the relevant organ per unit of tissue of the organ to be examined and per unit of time. For example, the flow also accurately and quantitatively indicates whether the blood circulation through the relevant organ is adequate. To the physician the flow constitutes a physical quantity that is valuable in determining whether or not the relevant organ functions correctly.

It is very well possible to measure the input and arrival profiles, that is to say the time-dependent concentrations of contrast agent in the artery and the veins of the patient, respectively, by means of X-ray computed tomography, by means of a magnetic resonance imaging method or on the basis of X-ray shadow images.

The invention also relates to a magnetic resonance imaging system which includes a data processor which is arranged to carry out the method according to the invention. The data processor is, for example a computer which is programmed so as to calculate the values of the perfusion quantities. The data processor may also include a special purpose processor which is provided with electronic circuits or integrated circuits especially designed for the calculation of the values of the perfusion quantities. A magnetic resonance imaging system according to the invention acquires magnetic resonance (MR) signals from at least a part of the body of the patient to be examined. Such MR signals are generated by arranging the patient in a magnetic field and by exciting spins, notably of the protons (hydrogen nuclei) in the body of the patient by means of an RF excitation pulse; the MR signals are emitted upon relaxation of the excited spins. In order to determine the perfusion quantities, the contrast agent is administered to the patient. First magnetic resonance signals are acquired from a part of the patient which contains the arteries wherein the contrast agent is pumped via the heart. The input profile is derived from these magnetic resonance signals. When the blood with the contrast agent reaches the part of the patient to be examined, for example the organ to be examined, for example (a part of) the brain, magnetic resonance signals are acquired again from this part to be examined. The arrival profile is derived from the magnetic resonance signals from the part of the patient to be examined. The data processor in the magnetic resonance imaging system according to the invention quickly and accurately calculates the values of the perfusion quantities from the MR signals. Consequently, the magnetic resonance imaging system according to the invention is particularly suitable for a quantitative study of perfusion of liquids through the tissue, for example the brain, of the patient.

These and other aspects of the invention are apparent from and will be elucidated, by way of example, on the basis of the following embodiments and with reference to the accompanying drawing; therein.

The FIGURE shows diagrammatically a magnetic resonance imaging system according to the invention.

The FIGURE shows diagrammatically a magnetic resonance imaging system 1 according to the invention. The magnetic resonance imaging system includes a receiving aerial for picking up the MR signals from the body of the patient. The patient 12 to be examined is arranged on an examination table 13 and moved into the examination space 14 of the magnetic resonance imaging system. The main magnetic field is applied in the examination space 14, so that the spins in the part of the patient which is situated in the examination space are oriented in the direction of the main magnetic field. Spins are excited, for example by generating an RF excitation pulse in the examination space. Application of a gradient field enables the excitation of spins exclusively in a selected part, for example a slice of the head of the patient. A read-out gradient and phase encoding gradient fields are applied during the relaxation of the spins so as to ensure that the MR signals are encoded in respect of the location of the spins producing the respective MR signals. Furthermore, due to differences in the relaxation of spins in different types of tissue within the patient differences arise between the signal levels of the MR signals. The encoding and the differences in signal levels enable the formation of a magnetic resonance image of the anatomy of the patient by means of the MR signals. Via a signal output 10, the MR signals are applied, possibly after a few signal processing operations for the correction of errors due to known error sources, to a signal processing unit 11. The signal processing unit 11 includes a reconstruction unit which derives an image signal (IS) from the corrected MR signals (cMR). The image signal (IS) represents, for example one or more cross-sectional images of a part of the brain of the patient 12 to be examined. The image signal (IS) is applied, for example, to a monitor 30 on which the image information of the cross-sectional image is displayed.

The corrected MR signals (cMR) are also applied to the data processor 2. The data processor 2 is arranged notably to calculate the values of the perfusion quantities from the corrected MR signals (cMR). To this end, the data processor is, for example, a suitably programmed computer; however, it may also be formed by a special purpose processor which is provided with electronic integrated circuits especially designed to calculate the perfusion quantities. In order to study the perfusion of liquid, such as blood, through, for example, the brain tissue of the patient to be examined, a contrast liquid is injected preferably into an artery of the patient. To this end, the magnetic resonance imaging system according to the invention includes an injector control unit 15 whereto an injection needle 16 for the injection is connected. The injector control unit 15 drives the injection needle so as to inject the contrast liquid in a predetermined, time-dependent concentration into the artery of the patient. When a magnetic resonance imaging system is used to record the dynamic input and arrival profiles, use is preferably made of a paramagnetic contrast agent, for example a contrast medium containing gadolinium. The injector control unit 15 is also connected to the data processor 2. The injector control unit 15 applies the time-dependent concentration profile, representing the time-dependent concentration of contrast agent injected into the patient, as a dynamic input profile (ip) to the data processor. The magnetic resonance imaging system according to the invention, however, can also suitably operate without the injector control unit 15; in the absence of the injector control unit, the dynamic input profile or time-averaged moments of the dynamic input profile are derived from the MR signals. To this end, MR signals are generated in the artery during the administration or injection of the contrast agent, so that the contrast agent is transported to the organ to be examined. For example, the reconstruction unit of the signal processing unit 11 forms a number of temporally successive MR images of the artery. The dynamic input profile is derived from the MR images of the artery by the data processor 2. The signal processing unit 11 then applies the dynamic input profile to the data processor 2.

Furthermore, the data processor 2 measures the dynamic arrival profile or time-averaged moments of the dynamic arrival profile. To this end, the magnetic resonance imaging system notably measures MR signals from a part of the body of the patient which contains blood vessels, notably veins, via which the injected contrast agent arrives. For example, MR signals are measured from a network of capillaries via which blood with contrast agent arrives in the brain. The time-dependent concentration of contrast agent which arrives in the part to be examined, for example the brain, is derived from these MR signals. Evidently, it is also possible for the reconstruction unit to form cross-sectional images which show the concentration of contrast medium injected into the artery or transported via the veins.

The data processor of the magnetic resonance imaging system according to the invention is also particularly suitable for calculating the perfusion quantities. The dynamic input profile, such as the time-dependent concentration of contrast agent supplied via the artery, will be referred to as a(t) hereinafter. The reference v(t) will be used to denote the dynamic arrival profile, such as the time-dependent concentration of contrast agent found in the part of the patient to be examined. There is also a convolution kernel r(t) which relates the dynamic arrival profile to the dynamic input profile in conformity with:

$$v(t) = \int_0^t a(t_1) r(t - t_1) dt_1 \tag{1}$$

It is to be noted, however, that according to the invention it is not necessary to know the convolution kernel r(t) exactly. Because of causality, of course, it holds that: r(t)=0 for t<0. The time averages, the zero-order moments, are expressed as $$V_v = \int_0^\infty v(t) dt, \quad V_a = \int_0^\infty a(t) dt, \quad V_r = \int_0^\infty r(t) dt. \tag{2}$$

It then holds that:

$$V_v = V_r V_a. \tag{3}$$

The quantities $V_a$ and $V_r$ are the input volume and the arrival volume, respectively. The average transit time of the contrast agent through the region to be examined is:

$$M_t = \frac{1}{V_v} \int_0^\infty t r(t) dt = \frac{V_{tr}}{V_v}. \tag{4}$$

The time-averaged first moments of the input profile and the arrival profile are:

$$A_t = \frac{1}{V_a} \int_0^\infty t a(t) dt = \frac{V_{ta}}{V_a} \text{ and } V_t = \frac{1}{V_v} \int_0^\infty t v(t) dt = \frac{V_{tv}}{V_v} \tag{5}$$

By transforming the integration variables and using equation (3) it is obtained that $$V_{tv} = V_{ta} V_r + V_{tr} V_a = V_v \left( \frac{V_{ta}}{V_a} + \frac{V_{tr}}{V_r} \right) \tag{6}$$

so that the average transit time can be readily calculated as $$M_t = A_t - V_t \tag{7}.$$

According to the invention the average transit time $M_t$ can be readily calculated as the difference between the first time-averaged moments of the dynamic input profile $A_t$ and the dynamic arrival profile $V_t$. The moments $A_t$ and $V_t$ can be derived either directly from the MR signals or from the dynamic input profiles a(t) and v(t). Because of the integration over time, it is not necessary to measure the input profiles particularly accurately in order to measure sufficiently accurate values of the moments such as $A_t$ and $V_t$.

The transit fraction rCBV is also calculated by the data processor 2 as $$rCBV = \frac{V_v}{V_a} \tag{8}$$

and the flow parameter $F_t$ is calculated by the data processor 2 in conformity with:

$$F_t = \frac{rCBV}{M_t} \tag{9}$$

The data processor 2 is also connected to a printer 31. The results of the calculations of the perfusion quantities, such as the average transit time, the transit fraction and the flow parameter, are applied to the printer in the form of perfusion signals (ps) representing the values of the perfusion quantities. The perfusion signals are, for example electronic or optical signals. The printer prints the values of the perfusion quantities on paper. The data processor is also connected to the monitor 30 and the perfusion signals are applied to the monitor 30 in order to display the values of the perfusion quantities on the monitor. For example, the data processor reproduces the spatial variation of the values of the perfusion quantities in the form of an image on the monitor. Such an image, representing the spatial variation of the perfusion quantities, is called a perfusion image. For example, the values of the perfusion quantities are encoded in (false) colors. The color distribution in the perfusion image then represents the spatial variations of the perfusion quantities. Furthermore, the data processor 2 may be connected to an information network 32, such as an intranet or a digital radiology information system, so as to supply the perfusion signals to the information network 32. A number of workstations 33 are connected to the information network 32. Via their own workstations which are remote from the magnetic resonance imaging system, various physicians can thus consult the values of the perfusion quantities and the perfusion images yielded by the examination.

What is claimed is:

1. A method of deriving a time-averaged moment of a convolution profile from dynamic input and arrival profiles, the arrival profile being related to the input profile according to convolution with the convolution profile, characterized in that a time-average moment of a dynamic input profile and a time-averaged moment of a dynamic arrival profile are determined, and that the time-averaged moment of the convolution profile is calculated from the time-averaged moments of the dynamic input profile and the time-averaged moments of the dynamic arrival profile.

2. A method as claimed in claim 1, characterized in that the time-averaged moment of the convolution profile is calculated from the time-averaged moments of the dynamic input profile and the time-averaged moments of the dynamic arrival profile by means of algebraic calculations.

3. A method as claimed in claim 2, characterized in that the time-averaged moment of the convolution profile is calculated as a rational function of the time-averaged moments of the dynamic input profile and of the time-averaged moments of the dynamic arrival profile.

4. A method as claimed in claim 1, characterized in that an input time is determined as the first time-averaged moment of the dynamic input profile, an arrival time is determined as the first time-averaged moment of the dynamic arrival profile, and that an average transit time is calculated as the difference between the input time and the arrival time.

5. A method as claimed in claim 1, characterized in that an input volume and an arrival volume are determined as the zero-order time-averaged moments of the dynamic input profile and the dynamic arrival profile, respectively, and that a transit fraction is calculated as the quotient of the arrival volume and the input volume.

6. A method as claimed in claim 1, characterized in that the input and arrival profiles are derived on the basis of magnetic resonance signals, notably on the basis of one or more magnetic resonance images.

7. A method as claimed in claim 1, characterized in that the input and arrival profiles are derived on the basis of absorption profiles measured by means of an X-ray computed tomography method, notably on the basis of one or more cross-sectional images reconstructed from the absorption profiles.

8. A method as claimed in claim 1, characterized in that the input and arrival profiles are derived on the basis of one or more X-ray images.

9. A magnetic resonance imaging system which includes a data processor which is arranged to carry out a method of deriving a time-averaged moment of a convolution profile from dynamic input and arrival profiles, the arrival profile being related to the input profile according to convolution with the convolution profile, characterized in that a time-averaged moment of a dynamic input profile and a time-averaged moment of a dynamic arrival profile are determined, and that the time-averaged moment of the convolution profile is calculated from the time-averaged moments of the dynamic input profile and the time-averaged moments of the dynamic arrival profile.

* * * * *